(12) United States Patent
Salmisuo et al.

(10) Patent No.: US 9,108,872 B2
(45) Date of Patent: Aug. 18, 2015

(54) SOLIDS SEPARATOR AND METHOD OF TREATMENT FOR BIOWASTE

(71) Applicant: STERIS Europe, Inc. Suomen Sivuliike, Tuusula (FI)

(72) Inventors: Mauri Salmisuo, Tuusula (FI); Juha Mattila, Porvoo (FI); Teppo Nurminen, Ojakkala (FI)

(73) Assignee: STERIS Europe, Inc. Suomen Sivuliike, Tuusula (FI)

( * ) Notice: Subject to any disclaimer, the term of this patent is extended or adjusted under 35 U.S.C. 154(b) by 0 days.

(21) Appl. No.: 14/280,719

(22) Filed: May 19, 2014

(65) Prior Publication Data

US 2014/0251923 A1  Sep. 11, 2014

Related U.S. Application Data

(62) Division of application No. 13/444,185, filed on Apr. 11, 2012, now Pat. No. 8,764,975.

(30) Foreign Application Priority Data

Apr. 12, 2011 (FI) .................................... 20115350

(51) Int. Cl.
| | | |
|---|---|---|
| A61L 11/00 | (2006.01) | |
| A61L 2/07 | (2006.01) | |
| B01D 35/18 | (2006.01) | |
| B01D 37/00 | (2006.01) | |
| C02F 11/12 | (2006.01) | |
| B09B 3/00 | (2006.01) | |

(52) U.S. Cl.
CPC ............... *C02F 11/128* (2013.01); *A61L 11/00* (2013.01); *B09B 3/0091* (2013.01)

(58) Field of Classification Search
None
See application file for complete search history.

(56) References Cited

U.S. PATENT DOCUMENTS

| | | | | |
|---|---|---|---|---|
| 2,432,317 | A | | 12/1947 | Lawson et al. .................. 210/93 |
| 2,626,709 | A | * | 1/1953 | Krieble .......................... 210/300 |
| 2,651,414 | A | | 9/1953 | Lawson et al. ................ 210/307 |
| 2,746,607 | A | * | 5/1956 | Hess ............................. 210/490 |
| 3,700,468 | A | * | 10/1972 | Shore ............................ 426/511 |
| 4,009,104 | A | | 2/1977 | Behrendt et al. .............. 210/744 |
| 4,089,781 | A | | 5/1978 | Asp ............................... 210/797 |
| 4,108,601 | A | | 8/1978 | Wolff ............................ 422/295 |
| 4,160,647 | A | | 7/1979 | Sendov et al. ................ 422/106 |
| 4,164,538 | A | | 8/1979 | Young et al. .................... 422/26 |

(Continued)

FOREIGN PATENT DOCUMENTS

DE  3338572  5/1985  ............ B01D 29/01

OTHER PUBLICATIONS

EPO Form 1570N—Search Report from corresponding European Patent App. No. 12397513.8; 5 pages.

*Primary Examiner* — Robert James Popovics
(74) *Attorney, Agent, or Firm* — Kusner & Jaffe

(57) ABSTRACT

The invention relates to a device and a method for the separation of solids from a biowaste slurry before heat treatment, and for heat treatment of the separated solids. The device comprises a chamber with a main inlet port for feeding slurry, and outlet ports. A unit for separating solids is adapted to an outlet port so, that liquid leaving the chamber has passed through the separation unit. A second outlet port is provided directly from the chamber to allow removal, following sterilization, of solids collected in the chamber. The sterilization is secured by temperature monitoring at representative locations.

7 Claims, 1 Drawing Sheet

(56) References Cited

U.S. PATENT DOCUMENTS

| | | | | |
|---|---|---|---|---|
| 4,166,096 | A | 8/1979 | Gillis et al. | 422/119 |
| 4,203,943 | A | 5/1980 | Gillis et al. | 422/27 |
| 4,203,947 | A | 5/1980 | Young et al. | 422/114 |
| 4,237,618 | A * | 12/1980 | Maffet | 34/386 |
| 4,239,730 | A | 12/1980 | Fahlvik et al. | 422/109 |
| 4,239,731 | A | 12/1980 | Gillis et al. | 422/112 |
| 4,284,600 | A | 8/1981 | Gillis et al. | 422/26 |
| 4,342,830 | A * | 8/1982 | Holloway | 435/161 |
| 4,592,847 | A | 6/1986 | Schumacher | 210/770 |
| 4,710,350 | A | 12/1987 | Petersen | 422/37 |
| RE32,695 | E | 6/1988 | Nahra et al. | 261/118 |
| 5,078,924 | A * | 1/1992 | Spinello | 264/500 |
| 5,091,158 | A | 2/1992 | Drauschke et al. | 422/295 |
| 5,106,594 | A * | 4/1992 | Held et al. | 422/292 |
| 5,114,596 | A | 5/1992 | Laterra | 210/798 |
| 5,119,994 | A * | 6/1992 | Placzek | 241/17 |
| 5,132,084 | A | 7/1992 | Harrell et al. | 422/26 |
| 5,217,688 | A | 6/1993 | Von Lersner | 422/26 |
| 5,294,412 | A * | 3/1994 | Orlando | 422/295 |
| 5,332,532 | A | 7/1994 | Kaye et al. | 588/16 |
| 5,362,443 | A * | 11/1994 | Tanaka et al. | 422/26 |
| 5,364,589 | A * | 11/1994 | Buehler et al. | 422/26 |
| 5,384,092 | A | 1/1995 | Sawhill et al. | 422/32 |
| 5,389,347 | A * | 2/1995 | Hall | 422/307 |
| 5,424,046 | A * | 6/1995 | Smith et al. | 422/295 |
| 5,454,953 | A | 10/1995 | Waibel | 210/664 |
| 5,470,546 | A * | 11/1995 | Hall | 422/292 |
| 5,480,547 | A * | 1/1996 | Williamson et al. | 210/533 |
| 5,480,610 | A | 1/1996 | Birkholz et al. | 422/26 |
| 5,540,846 | A | 7/1996 | Koch et al. | 210/741 |
| 5,547,582 | A | 8/1996 | Waibel | 210/664 |
| 5,570,845 | A * | 11/1996 | Lewis et al. | 241/21 |
| 5,628,916 | A | 5/1997 | Stevens et al. | 210/798 |
| 5,666,878 | A | 9/1997 | Taricco | 100/73 |
| 5,687,755 | A | 11/1997 | Farquhar et al. | 137/182 |
| 5,695,650 | A * | 12/1997 | Held | 210/748.01 |
| 5,737,918 | A * | 4/1998 | Khinsky et al. | 60/297 |
| 5,759,491 | A | 6/1998 | Bunin | 422/38 |
| 5,799,883 | A | 9/1998 | Lewis et al. | 241/21 |
| 5,830,419 | A * | 11/1998 | Held et al. | 422/307 |
| 5,880,438 | A | 3/1999 | Parrini et al. | 219/519 |
| 5,906,800 | A | 5/1999 | Napierkowski et al. | 422/298 |
| 5,941,468 | A * | 8/1999 | Lewis et al. | 241/17 |
| 5,945,006 | A | 8/1999 | Mignani | 210/797 |
| 5,997,733 | A | 12/1999 | Wilbur et al. | 210/85 |
| 5,997,813 | A | 12/1999 | Yaskoff et al. | 422/26 |
| 6,036,862 | A | 3/2000 | Stover | 210/603 |
| 6,097,015 | A | 8/2000 | McCullough et al. | 219/686 |
| 6,113,854 | A | 9/2000 | Milum et al. | 422/32 |
| 6,180,070 | B1 | 1/2001 | Benson | 422/26 |
| 6,248,985 | B1 * | 6/2001 | Tomasello | 219/679 |
| 6,332,977 | B1 | 12/2001 | Janecek | 210/96.1 |
| 6,379,613 | B1 | 4/2002 | Stempf | 422/26 |
| 6,397,492 | B1 * | 6/2002 | Malley | 34/411 |
| 6,437,211 | B2 | 8/2002 | Kaye et al. | 588/318 |
| 6,458,240 | B1 * | 10/2002 | Bouchette et al. | 162/4 |
| 6,472,580 | B2 * | 10/2002 | Kaye et al. | 588/317 |
| 6,521,135 | B1 | 2/2003 | Benesi | 210/771 |
| 6,660,164 | B1 | 12/2003 | Stover | 210/612 |
| 6,716,401 | B2 * | 4/2004 | Benson | 422/297 |
| 6,886,698 | B2 | 5/2005 | Tully | 210/452 |
| 6,890,129 | B2 | 5/2005 | Fabbri | 406/106 |
| 6,926,874 | B2 | 8/2005 | Ongaro | 422/298 |
| 6,959,504 | B2 | 11/2005 | Fabbri | 34/380 |
| 7,011,741 | B2 | 3/2006 | Benesi | 210/97 |
| 7,183,453 | B2 | 2/2007 | Wilson et al. | 588/318 |
| 7,211,229 | B2 | 5/2007 | Halli et al. | 422/307 |
| 7,347,391 | B2 * | 3/2008 | Michalek et al. | 241/23 |
| 7,381,323 | B2 | 6/2008 | Umezawa et al. | 210/108 |
| 7,445,716 | B2 | 11/2008 | Quintel et al. | 210/636 |
| 7,497,340 | B2 | 3/2009 | Hershberger et al. | 210/435 |
| 7,611,604 | B2 | 11/2009 | Salmisuo et al. | 159/49 |
| 7,621,898 | B2 | 11/2009 | Lalomia et al. | 604/319 |
| 7,641,852 | B1 | 1/2010 | McPhail et al. | 422/26 |
| 7,767,142 | B1 * | 8/2010 | Smith et al. | 422/37 |
| 7,812,206 | B2 | 10/2010 | Wilsak et al. | 585/814 |
| 7,815,808 | B2 | 10/2010 | Benesi et al. | 210/741 |
| 7,829,755 | B2 | 11/2010 | Wilson et al. | 588/319 |
| 7,857,980 | B2 | 12/2010 | Bellussi | 210/742 |
| 7,910,788 | B2 | 3/2011 | Wilson et al. | 588/318 |
| 8,066,953 | B2 | 11/2011 | Muth | 422/198 |
| 8,201,695 | B2 | 6/2012 | Kang et al. | 210/350 |
| 8,206,660 | B2 | 6/2012 | Buczynski et al. | 422/296 |
| 8,211,319 | B2 | 7/2012 | Wilsak et al. | 210/767 |
| 8,309,711 | B2 | 11/2012 | Wiley | 536/127 |
| 8,409,429 | B2 | 4/2013 | Kaske | 210/86 |
| 8,470,182 | B2 | 6/2013 | Muth | 210/749 |
| 8,764,975 | B2 * | 7/2014 | Salmisuo et al. | 210/104 |
| 2001/0009969 | A1 | 7/2001 | Kaye et al. | 588/205 |
| 2001/0053869 | A1 | 12/2001 | Kaye et al. | 588/200 |
| 2003/0007914 | A1 | 1/2003 | Ongaro | 422/292 |
| 2003/0007915 | A1 | 1/2003 | Ongaro | 422/297 |
| 2003/0040651 | A1 | 2/2003 | Wilson et al. | 585/240 |
| 2003/0147771 | A1 * | 8/2003 | Hodgins | 422/26 |
| 2004/0018112 | A1 | 1/2004 | Wilson et al. | 422/3 |
| 2004/0026312 | A1 | 2/2004 | Tully | 210/452 |
| 2004/0141877 | A1 * | 7/2004 | Devine et al. | 422/32 |
| 2004/0168986 | A1 | 9/2004 | Katano | 210/695 |
| 2004/0208784 | A1 | 10/2004 | Matsuda et al. | 422/38 |
| 2005/0002824 | A1 | 1/2005 | Halli et al. | 422/3 |
| 2005/0145567 | A1 | 7/2005 | Quintel et al. | 210/636 |
| 2005/0189303 | A1 | 9/2005 | Kaeske | 210/774 |
| 2006/0027509 | A1 | 2/2006 | Benesi et al. | 210/770 |
| 2006/0102292 | A1 | 5/2006 | Salmisuo et al. | 159/49 |
| 2006/0222574 | A1 | 10/2006 | Kaye et al. | 422/184.1 |
| 2006/0247485 | A1 | 11/2006 | Wilson et al. | 588/299 |
| 2007/0038013 | A1 | 2/2007 | Wilson et al. | 588/318 |
| 2007/0175825 | A1 | 8/2007 | Denney | 210/631 |
| 2007/0199903 | A1 | 8/2007 | Denney | 210/723 |
| 2007/0218541 | A1 | 9/2007 | Denney et al. | 435/267 |
| 2007/0221552 | A1 | 9/2007 | Denney | 210/85 |
| 2008/0078726 | A1 | 4/2008 | Pancaldi et al. | 210/770 |
| 2008/0138253 | A1 | 6/2008 | Golder et al. | 422/112 |
| 2009/0050581 | A1 | 2/2009 | Kaske | 210/797 |
| 2009/0101601 | A1 | 4/2009 | Kaske | 210/798 |
| 2009/0105517 | A1 | 4/2009 | Kaye et al. | 588/318 |
| 2009/0137858 | A1 | 5/2009 | Wilson et al. | 588/318 |
| 2010/0237289 | A1 * | 9/2010 | Self et al. | 252/373 |
| 2011/0031192 | A1 | 2/2011 | Wiley | 210/770 |
| 2011/0040138 | A1 | 2/2011 | Wilson et al. | 588/317 |
| 2011/0048086 | A1 | 3/2011 | Kaye et al. | 71/14 |
| 2011/0171073 | A1 | 7/2011 | Wilson et al. | 422/108 |
| 2012/0003120 | A1 * | 1/2012 | Mattila | 422/38 |
| 2012/0059603 | A1 | 3/2012 | Stering | 702/47 |
| 2012/0267323 | A1 * | 10/2012 | Salmisuo et al. | 210/766 |
| 2012/0301356 | A1 | 11/2012 | Olson et al. | 422/33 |
| 2013/0084225 | A1 | 4/2013 | Buczynski | 422/292 |
| 2013/0108506 | A1 * | 5/2013 | De La Fuente Munoz | 422/26 |
| 2013/0236392 | A1 | 9/2013 | Naterer et al. | 423/648.1 |
| 2014/0037495 | A1 | 2/2014 | Ahiska et al. | 422/3 |
| 2014/0251923 | A1 * | 9/2014 | Salmisuo et al. | 210/742 |

* cited by examiner

SOLIDS SEPARATOR AND METHOD OF TREATMENT FOR BIOWASTE

RELATED APPLICATIONS

This application is a divisional U.S. application Ser. No. 13/444,185, filed Apr. 11, 2012, which claims priority from Finland Patent Application No. 20115350, filed Apr. 12, 2011, said patent applications hereby fully incorporated herein by reference.

FIELD OF THE INVENTION

The invention relates to the field of sterilization of biological waste. More particularly, the invention relates to a device and a method for the separation of solids from a slurry before heat treatment, and for heat treatment of the separated solids.

BACKGROUND OF THE INVENTION

Biological waste in the form of liquids and suspensions is produced e.g. in hospitals, agricultural or biological research and production facilities, plasma fractionation facilities, etc. Biological wastes produced in such facilities cannot be directly conducted to a sewer system, as these wastes often contain micro-organisms, such as bacteria, viruses, germs and the like, which are hazardous to humans and animals. Prior to conducting to a sewer system, such biowaste must first be deactivated in a treatment plant designed for this purpose. For the treatment of biowaste, different treatment plants have been designed in which biowaste is sterilized prior to conducting to the sewer system. The sterilization of biowaste can be carried out chemically or by means of heat. The treatment plants can operate continuously or batchwise.

Sterilization in the context of the present discussion includes the killing of microbes including bacteria and viruses so as to render them non-pathogenic, as well as the destruction of other biological agents that may cause harmful effects.

A typical thermal continuous biowaste sterilisation apparatus comprises a separating unit for solid matter, a storage tank, a heating unit and a dwell circuit as well as a circulation circuit for circulating biowaste through said heating unit and said dwell circuit.

Separation of solid matter from a biowaste suspension or slurry is necessary in order not to cause clogging of the system or excessive scaling of heat transfer surfaces. Biowaste slurries may contain considerable amounts of solids. As the separated solids also constitute a biological hazard, they must be separately and reliably sterilized, by way of e.g. heat treatment, before being disposed of.

SUMMARY OF THE INVENTION

According to the present invention, a device is provided for the reliable separation and sterilization of solids of a given dimension from a biowaste slurry. The device comprises a chamber with a main inlet port and first and second main outlet ports. A unit for separating solids, preferably a filter or screen unit, is adapted to the first main outlet port so, that liquid leaving the chamber will pass through the solids separating unit. A second outlet port is provided directly from the chamber to allow removal of solids collected in the chamber. Means for temperature measurement are provided at representative locations to ensure that sterilizing conditions have been reached in all parts of the solids contained in the device. Preferably, such means comprise temperature sensors connected to a control system.

During operation, solids are separated from the feed stream and remain in the chamber. In the case the separation device is a filter or screen, it is preferably periodically back flushed using steam to ensure sufficient throughput. When the chamber capacity is reached, the feed is stopped, valves are set to appropriate positions and the collected batch of solids is sterilized within the chamber, preferably using heat treatment. Discharge of the sterilized solids takes place through the second main outlet port.

According to a further embodiment of the invention, the mechanical separation device is a cyclone.

According to a second aspect of the present invention, a method is provided for separating solid material from a biowaste suspension and subsequently sterilizing said solid material, comprising the steps of conducting a suspension of biowaste into a chamber, conducting the suspension out of the chamber through a mechanical separation device thereby separating solid particles from the suspension, essentially draining the liquid part of the suspension from the chamber, raising the temperature of the solid material remaining in the chamber by means of direct steam injection to a predetermined sterilization temperature, maintaining said sterilization temperature for a predetermined period of time, and removing the sterilized solid material from the chamber.

The addition of a base to the material to be sterilized may be used as a supplement to steam injection. Examples are alkali metal hydroxides.

Preferably, the sterilized solid material is cooled and the chamber flushed in connection with the removal step.

DETAILED DESCRIPTION OF PREFERRED EMBODIMENT

Figure 1:
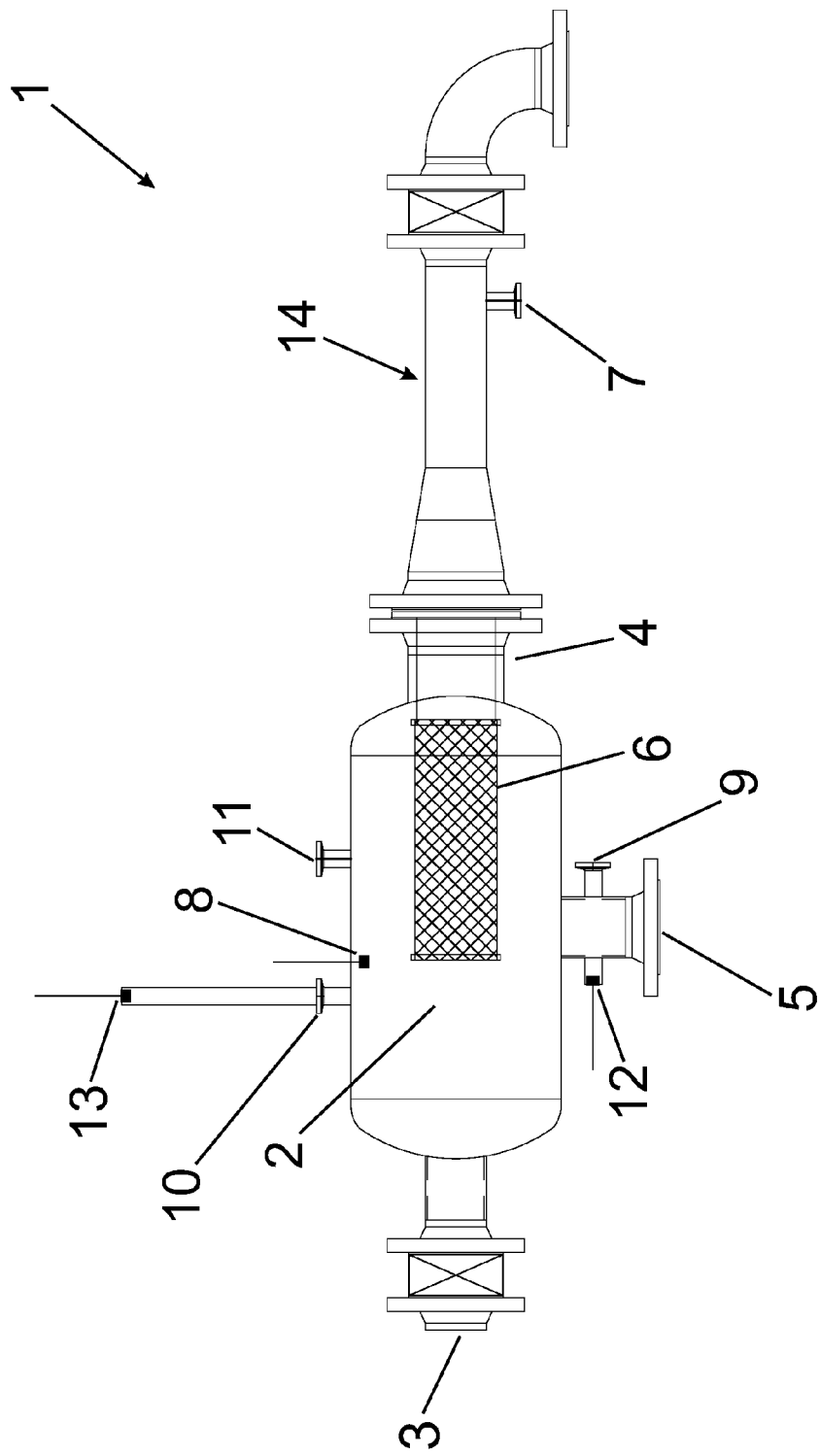
FIG. 1 is a sectional side view of a device according to the invention.

The invention will now be described in detail with reference to the accompanying drawing. In FIG. 1 is shown a sectional side view of a device 1 in accordance with the invention. Chamber 2 is provided with main inlet port 3, first main outlet port 4 and second main outlet port 5. These are fitted with valves. A control system, not shown, is normally provided for controlling and monitoring the operation of the device.

During operation, biowaste slurry is fed into the chamber through main inlet port 3, preferably by pumping. The valve on second main outlet port 5 is closed, and liquid is forced through filter or screen unit 6 and leaves through first main outlet port 4, whose outlet valve is open. The filter or screen unit 6 is dimensioned to retain solid particles according to required specifications. For example, the filter may be designed to retain particles of more than 1 mm diameter. The filter is of a type withstanding sterilization temperatures repeatedly without replacement need. The chamber is a pressure vessel preferably rated for at least 3.1 bar pressure and at least +144° C. temperature. Pressure and/or temperature ratings are dependent on the required sterilization temperature set point.

The filtered phase may be collected in a buffer tank for further heat treatment in a plant as disclosed in e.g. European Patent 1 440 040.

To keep the filter unit open, steam may be periodically supplied through connection 7 with a pressure sufficient to detach a filter cake possibly forming on the upstream filter surface. Intervals of 1 to 5 minutes with a flushing period of 5-30 seconds may be used. A level indicator (not shown) may be used to monitor the need for back flushing.

The filter unit and chamber are dimensioned to separate and hold a volume of solids determined by the capacity requirements of the heat treatment plant. For example, a chamber of about 30 l operational volume may be used. The point when the capacity of the chamber has been reached may be indicated by level switch 8. Subsequently, the valves of the main inlet port 3 and main outlet ports 4, 5 are closed. A sterilization operation may then be carried out, preferably under the supervision of the control system. A sterilization temperature set point and exposure period are set, e.g. 130° C. for 20 minutes.

Sterilization steam (e.g. plant steam at 2.5 bar supply pressure) is supplied both through the filter 6 via connection 7 and through the lowest point of the chamber via connection 9 on a branch of second main outlet port 5. Condensate leaves through outlet port 10, preferably connected to the buffer tank of the downstream heat treatment plant, thus ensuring proper sterilization also of any entrained material.

The sterilization temperature is monitored using a measurement sensor 12 at connection 9, and coldest point measurement 13 at the far end of the condensate line. Both of the sensor readings must be above the set temperature for the sterilization conditions to be accepted by the control system. When both temperature sensors have reached set point, the sterilization exposure period begins. Preferably, the first sensor is located at the bottom of the solid load and the second is located close to the steam trap in the outlet pipe to provide a representative result for sterilization, showing that the required temperature has been reached throughout the load. The sterilization process can be validated by a microbiological challenge test using e.g. *Geobacillus Stearothermophilus* spores in a sterilization sequence, to prove an overkill result of min. $10^6$ population reduction.

After the exposure period, the program of the control system proceeds to a cooling step. During this step, all valves remain closed and steam supply is stopped. The program waits for the temperatures at both measuring points to fall e.g. below +90° C.

When a temperature of +90° C. is reached, the program proceeds to an emptying and rinse-discharge step. During this step, the second main outlet port 5 functions as a solids discharge port. The valve of second main outlet port 5 is opened and the valve on rinse water inlet 11 opens, e.g. for a period of 60 to 120 seconds, to clean the chamber and to convey all of the decontaminated solids through the second main outlet port to the drain.

Advantageously, a spool piece 14 is adapted in the filtrate discharge line to facilitate service and replacement of the filter unit. Removal of the spool piece allows removal of the filter through outlet port 4.

Advantageously, two units may be connected in parallel to maintain continuous operation if one unit reaches maximum capacity and proceeds to the sterilization and discharge steps.

The sterilization of solid material by injection of steam directly into the material is highly efficient compared to the heating of a volume of liquid in which the corresponding material is suspended.

The above detailed description is to be taken as an example, not limiting the invention relative to the patent claims.

Having described the invention, the following is claimed:

1. A method for separating batches of solid material from a liquid slurry including biologically hazardous material and for sterilizing separated solid material, said method comprising the steps of:
    introducing said slurry into a chamber of a pressure vessel having a filter or a screen extending thereinto and being in fluid communication with a first main valved outlet port of said chamber, for separating solid material in said slurry from liquid in said slurry;
    allowing liquid in said slurry to pass through said filter or screen and be discharged from said chamber;
    fluidly isolating said chamber from a surrounding environment after said liquid has been discharged from said chamber;
    after fluidly isolating said chamber, injecting steam into said chamber wherein said steam contacts said solid material remaining in said chamber to heat said solid material to a predetermined sterilization temperature and conveying a condensate out of said chamber;
    maintaining said predetermined sterilization temperature for a predetermined period of time; and
    removing sterilized solid material from said chamber.

2. The method according to claim 1, wherein the temperature is monitored at at least two locations.

3. The method according to claim 1, wherein a base is added to the material which is to be sterilized.

4. The method according to claim 1, wherein said step of removing sterilized solid material from the chamber includes conveying rinse water through said chamber.

5. The method according to claim 1, wherein said chamber includes:
    a main valved inlet port for conveying said slurry into said chamber;
    a second main valved outlet port for conveying said sterilized solid material out of said chamber; and
    a condensate line for conveying said condensate out of said chamber.

6. The method according to claim 5, wherein a first temperature sensor is disposed in said second main valved outlet port and a second temperature sensor is disposed in said condensate line, said first temperature sensor and said second temperature sensor for measuring temperatures in said chamber during said step of maintaining said sterilization temperature for a predetermined period of time.

7. The method according to claim 5, wherein said step of fluidly isolating said chamber from a surrounding environment includes closing said main valved inlet port, said second main valved outlet port and a valved filtrate discharge line connected to said first main outlet port.

\* \* \* \* \*